(12) United States Patent
Lofer et al.

(10) Patent No.: US 9,910,303 B2
(45) Date of Patent: Mar. 6, 2018

(54) DEVICE FOR PRODUCING AND TESTING ELECTRICAL SWITCHABLE GLASSES AND METHOD OF DOING THE SAME

(71) Applicant: GAUZY LTD., Tel-Aviv (IL)

(72) Inventors: Adrian Lofer, Kfar Saba (IL); Eyal Peso, Bat Yam (IL); Dimitri Dobrenko, Raanana (IL); Yair Asulin, Raanana (IL)

(73) Assignee: GAUZY LTD., Tel-Aviv (IL)

( * ) Notice: Subject to any disclaimer, the term of this patent is extended or adjusted under 35 U.S.C. 154(b) by 0 days.

(21) Appl. No.: 15/309,262

(22) PCT Filed: May 4, 2015

(86) PCT No.: PCT/IL2015/050461
§ 371 (c)(1),
(2) Date: Nov. 7, 2016

(87) PCT Pub. No.: WO2015/170318
PCT Pub. Date: Nov. 12, 2015

(65) Prior Publication Data
US 2017/0075152 A1    Mar. 16, 2017

Related U.S. Application Data

(60) Provisional application No. 61/990,120, filed on May 8, 2014.

(51) Int. Cl.
*F23Q 23/08* (2006.01)
*G02F 1/13* (2006.01)
(Continued)

(52) U.S. Cl.
CPC .............. *G02F 1/1309* (2013.01); *E06B 9/24* (2013.01); *G01N 21/47* (2013.01); *G02F 1/1334* (2013.01); *E06B 2009/247* (2013.01)

(58) Field of Classification Search
CPC ..... G02F 1/1309; G02F 1/1334; G01N 21/47; E06B 9/24; E06B 2009/247
See application file for complete search history.

(56) References Cited

U.S. PATENT DOCUMENTS 4,934,423 A     6/1990  Withrow
5,459,594 A  * 10/1995  Nakanishi ............. G02F 1/1309
                                                        324/756.01
(Continued)

FOREIGN PATENT DOCUMENTS

WO     2015/170318 A2    11/2015

OTHER PUBLICATIONS

International Search Report for PCT/IL2015/050461, dated Nov. 2, 2015.
(Continued)

*Primary Examiner* — Donald Raleigh (57) ABSTRACT

Electrical switchable glasses production comprising the steps of: (a) providing a first and second cover glass; (b) providing a PDLC or other electrically switchable film; (c) providing a first and second layer of adhesive interlayer; (d) providing a PDLC inspection station further comprising: (i) a levelled-up table; (ii) means for inspecting properties of the PDLC film and/or glasses selected from the group consisting of electric properties, optical properties, mechanical properties and any combination thereof; (e) placing the first cover glass onto the levelled-up table; (f) spreading a first layer of adhesive interlayer (g) spreading the PDLC film over the previously placed adhesive interlayer; (h) spreading a second layer of adhesive interlayer; (i) covering the PDLC film by means of the second cover glass; (j) laminating the PDLC film between the first and second cover glasses; and
(Continued)

(k) inspecting the glass properties by means of the PDLC inspection station before and after laminating the PDLC film.

15 Claims, 11 Drawing Sheets (51) Int. Cl.
*G02F 1/1334* (2006.01)
*E06B 9/24* (2006.01)
*G01N 21/47* (2006.01)

(56) References Cited

U.S. PATENT DOCUMENTS

| | | |
|---|---|---|
| 6,982,178 B2 | 1/2006 | LeCain et al. |
| 2004/0001177 A1* | 1/2004 | Byun .................... G02F 1/1339 349/187 |
| 2012/0169987 A1 | 7/2012 | Li et al. |
| 2012/0307337 A1 | 12/2012 | Bartug et al. |
| 2013/0272833 A1 | 10/2013 | Duncan et al. |
| 2013/0321744 A1 | 12/2013 | Lin et al. |
| 2015/0085200 A1* | 3/2015 | Choi ..................... G02F 1/1309 349/1 |
| 2015/0301366 A1* | 10/2015 | Gayout ............. B32B 17/10504 349/86 |

OTHER PUBLICATIONS

Written Opinion of the International Search Authority for PCT/IL2015/050461, dated Nov. 2, 2015.
International Preliminary Report on Patentability, Chapter II, for PCT/IL2015/050461, dated May 3, 2016.

\* cited by examiner

DEVICE FOR PRODUCING AND TESTING ELECTRICAL SWITCHABLE GLASSES AND METHOD OF DOING THE SAME

CROSS-REFERENCE TO RELATED APPLICATIONS

This application is a U.S. National Phase filing under 35 U.S.C. 371 of International (PCT) Patent Application No. PCT/IL2015/050461, filed 4 May 2015, which claims priority from U.S. Provisional Patent Application No. 61/990,120, filed 8 May 2014, both of which are incorporated by reference in their entirety.

FIELD OF THE INVENTION

The present invention relates to quality assessment methods and devices, and, more specifically, to quality assessment concerning electric switchable devices.

BACKGROUND OF THE INVENTION

Switchable glass or switchable windows in its application to windows or skylights refer to glass or glazing that changes light transmission properties when voltage, light or heat is applied.

The aforesaid glasses or windows control an amount of light (and thereby heat) transmission. When activated, the glass changes from transparent to non-transparent and blocks some or all wavelengths of light. Different mechanisms such as electro-chromic, photochromic, thermo-chromic, suspended particle, micro-blind and liquid crystal can be used.

Specifically, in polymer dispersed liquid crystal devices (PDLCs), liquid crystals are dissolved or dispersed into a liquid polymer followed by solidification or curing of the polymer. During the change of the polymer from a liquid to solid, the liquid crystals become incompatible with the solid polymer and form droplets throughout the solid polymer. The curing conditions affect the size of the droplets that in turn affect the final operating properties of the "smart window". Typically, the liquid mix of polymer and liquid crystals is placed between two layers of glass or plastic having a thin layer of a transparent, conductive material followed by curing of the polymer, thereby forming the basic sandwich structure of the smart window. This structure is in effect a capacitor.

Electrodes from a power supply are attached to the transparent electrodes. With no applied voltage, the liquid crystals are randomly arranged in the droplets, resulting in scattering of light as it passes through the smart window assembly. This results in non-transparent appearance.

When a voltage is applied to the electrodes, the electric field formed between the two transparent electrodes on the glass causes the liquid crystals to align, allowing light to pass through the droplets with very little scattering and resulting in a transparent state. The degree of transparency can be controlled by the applied voltage. This is possible because at lower voltages, only a few of the liquid crystals align completely in the electric field, so only a small portion of the light passes through while most of the light is scattered. As the voltage is increased, fewer liquid crystals remain out of alignment, resulting in less light being scattered. It is also possible to control the amount of light and heat passing through, when tints and special inner layers are used. It is also possible to create fire-rated and anti X-Ray versions for use in special applications. Most of the devices offered today operate in on or off states only, even though the technology to provide for variable levels of transparency is easily applied. This technology has been used in interior and exterior settings for privacy control (for example conference rooms, intensive-care areas, bathroom/shower doors) and as a temporary projection screen. It is commercially available in rolls as adhesive backed Smart film that can be applied to existing windows and trimmed to size in the field.

Conventional practice in quality assessment of the switchable PDLC glass is in inspection of electrical, optical and mechanical properties of end products which are rejected because of electric or optical defects of PDLC film laminated between the two glass plates. Defect correction after lamination is impossible. There is a long-felt and unmet need to provide a method of step-by-step operation checking switchable PDLC glasses directed to reduction of rejection rate.

SUMMARY OF THE INVENTION

It is hence one object of the invention to disclose a method of producing electric switchable devices. The aforesaid method comprises the steps of: (a) providing a first cover glass and a second cover glass; (b) providing a PDLC film or any other electrically switchable film; (c) providing a first layer of adhesive interlayer and a second layer of adhesive interlayer; (d) providing an inspection station further comprising: (i) a levelled-up table; (ii) means for inspecting properties of said electric switchable devices selected from the group consisting of electric properties, optical properties, mechanical properties and any combination thereof; (e) placing said first cover glass onto said levelled-up table; (f) spreading a first layer of adhesive interlayer; (g) spreading said PDLC film over the previously placed adhesive interlayer; (h) spreading a second layer of adhesive interlayer; (i) covering said PDLC film by means of said second cover glass; (j) laminating said PDLC film between said first and second cover glasses; and (k) inspecting said glass properties by means of said PDLC inspection station.

It is a core purpose of the invention to provide the inspecting step is performed before and after said step of laminating said electric switchable film and also it is possible to test the glass panels during installation.

Another object of the invention is to disclose the method comprising a step of projecting extension bars configured for supporting oversized electric switchable devices.

A further object of the invention is to disclose the method comprising a step of tilting said electric switchable devices.

A further object of the invention is to disclose the step of inspecting mechanical properties comprising visually inspecting a glass surface and measuring glass overall dimensions.

A further object of the invention is to disclose the step of inspecting optical properties comprising measuring optical transmittance/haze of the electric switchable device and uniformity thereof over said electric switchable device.

A further object of the invention is to disclose the step of inspecting optical properties comprising inspecting a haze degree by means of measuring a time resolved spectral dependence of transmittance pertaining to said electric switchable device.

A further object of the invention is to disclose the step of inspecting optical properties comprising illuminating said electric switchable device by backlight LED.

A further object of the invention is to disclose the step of illuminating said electric switchable device by backlight performed by mean of a light source selected from the group consisting of a white light source, a white light source provided with a spectral filter, a laser and any combination thereof.

A further object of the invention is to disclose the step of inspecting optical properties is performed by at least 5 sensors distributed over a surface of the electric switchable device.

A further object of the invention is to disclose the step of inspecting optical properties performed by means of line-by-line scanning.

A further object of the invention is to disclose the step of inspecting optical properties comprising inspecting specific pixels of the electric switchable film or laminated glass performed by microscopic means. A further object of the invention is to disclose the step of inspecting electric properties comprising measuring values of electric current, resistance, capacitance and power consumption.

A further object of the invention is to disclose the step of measuring values of electric current, resistance, capacitance and power consumption performed by a square wave 70 VAC at frequency ranging between 25 and 50 Hz.

A further object of the invention is to disclose the step first energizing said electric switchable device by means of an initial ramp-up train of pulses.

A further object of the invention is to disclose the initial ramp-up comprising a pulse train of increasing amplitude; pulses of said train are characterized by changeable pulse duration and time interval therebetween.

A further object of the invention is to disclose the method in which the electric switchable device is prevented from applying DC voltage.

A further object of the invention is to disclose the method comprising a step of authenticating said electric switchable device.

A further object of the invention is to disclose the step of authenticating said electric switchable device performed by means of recognizing a label identifier on a surface of said electric switchable device or embedded into said electric switchable device.

A further object of the invention is to disclose the label identifier, which is an electromagnetically detectable label.

A further object of the invention is to disclose the label identifier selected from the group consisting of an RFID tag, a computer chip, a graphic label on a surface of said electric switchable device or therewithin, which is detectable visually and/or instrumentally.

A further object of the invention is to disclose the step of authenticating said electric switchable device comprising real time reporting malfunction incidents to a manufacturer server in a wireless manner.

A further object of the invention is to disclose the step of inspecting electric properties performed before installing said electric switchable device in situ. A further object of the invention is to disclose a method of quality assurance producing electric switchable devices; said method comprising the steps of: (a) providing an electric switchable device; (b) providing an inspection station further comprising: (i) a test table; (ii) means for inspecting properties of said electric switchable devices selected from the group consisting of electric properties, optical properties, mechanical properties and any combination thereof during production and during installation on site; (c) placing said glass onto said table; (d) inspecting said properties by means of said inspection station.

A further object of the invention is to disclose a test station for inspection of an electric switchable device operative in the method of providing a first cover glass and a second cover glass; providing a PDLC film or any other electrically switchable film; providing a first layer of adhesive interlayer and a second layer of adhesive interlayer; providing an inspection station further comprising: a levelled-up table; means for inspecting properties of said electric switchable devices selected from the group consisting of electric properties, optical properties, mechanical properties and any combination thereof; placing said first cover glass onto said levelled-up table; spreading a first layer of adhesive interlayer; spreading said PDLC film over said previously placed adhesive interlayer; spreading a second layer of adhesive interlayer; covering said PDLC film by means of said second cover glass; laminating said PDLC film between said first and second cover glasses; and inspecting said glass properties by means of said PDLC inspection station; wherein said inspecting step is performed before and after said step of laminating said electric switchable film.

A further object of the invention is to disclose a test station for inspection of an electric switchable device operative in the method of providing an electric switchable device; providing an inspection station further comprising: a test table; means for inspecting properties of said electric switchable devices selected from the group consisting of electric properties, optical properties, mechanical properties and any combination thereof; placing said glass onto said table; inspecting said properties by means of said inspection station; wherein said inspecting step is performed before and after said step of laminating said electric switchable film.

A further object of the invention is to disclose a test station for inspection of an electric switchable device operative in any of the above-mentioned methods and combination thereof.

A further object of the invention is to disclose a handheld installation device aim to test the electric switchable device on the installation site before glazing the glass panel.

BRIEF DESCRIPTION OF THE DRAWINGS

In order to understand the invention and to see how it may be implemented in practice, a plurality of embodiments will now be described, by way of non-limiting example only, with reference to the accompanying drawings, in which.

DETAILED DESCRIPTION OF THE INVENTION

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a method of producing electrical switchable devices.

The term "electrical switchable device" hereinafter refers to a polymer dispersed liquid crystal film or glass including a polymer dispersed (among them low-molar-mass) liquid crystal film or glass abbreviated as PDLC, PDSLC, PDCLC and PDNLC, respectively. Suspended particle and electrochromic devices are in the scope of the abovementioned definition.

A test station of the present invention is designed for quality verification functional inspection within production process of electric switchable devices. The purpose of the previously mentioned inspection is to keep faulty products to minimum. Electric and optical properties of each produced electric switchable device are characterized and documented in an individual manner.

The test station comprises a test table designed for supporting the electric switchable device to be tested during quality inspection. The previously mentioned table constitutes a frame structure with extension bars for supporting electric switchable devices of bigger sizes. Thus, according to the presented invention, the electric switchable devices of any size can be tested on the disclosed test station.

For convenience of visual control, the test table is designed for tilting the supported electric switchable device. For this reason, a tiltable portion of the table is provided with a counter balancer to provide smoothness of tiltable portion.

As mentioned above, the test station is designed for characterization of the electric switchable devices concerning optical properties. Spectral dependence of optical transmittance/haze degree is measured by at least 5 sensors distributed over a surface of the electric switchable device. Line-by-line scanning of the optical properties of the electric switchable devices is also in the scope of the present invention. Optical transmittance/haze degree can be measured in both white and monochromatic light. For this reason, conventional light sources with spectral filters and lasers can be used. The test station can be provided with microscopic means designed for testing a specific pixel of the electric switchable film or laminated glass. The test station is also configured for time resolved optical characteristic of the electric switchable devices for characterization of change in optical transmittance/haze degree in response to applying AC square voltage pulse sequence.

Any electric switchable device produced according to the present invention has a unique label identifier embedded inside which is detectable visually or instrumentally. The previously mentioned identifier dually functions in passive and active modes. In passive mode, the visually or instrumentally readable identifier carries data concerning operability and/or malfunction history of electric switchable devices. In active mode, the identifier is configured for transmitting data concerning operability and/or malfunction to a server of the manufacturer. According to present invention, the manufacturer commands comprehensive information in real time and can provide better service with lower operation costs and extend a warrant/assurance scope. Thus, electric switchable device history is documented belongs to a specific article and is independent on a specific contractor dealing with electric switchable device mounting and maintenance. The described function can be implemented by means of embedded switchable RFID tag or computer chip replying for an outer query or transmitting data to the manufacturer server.

Figure 1:
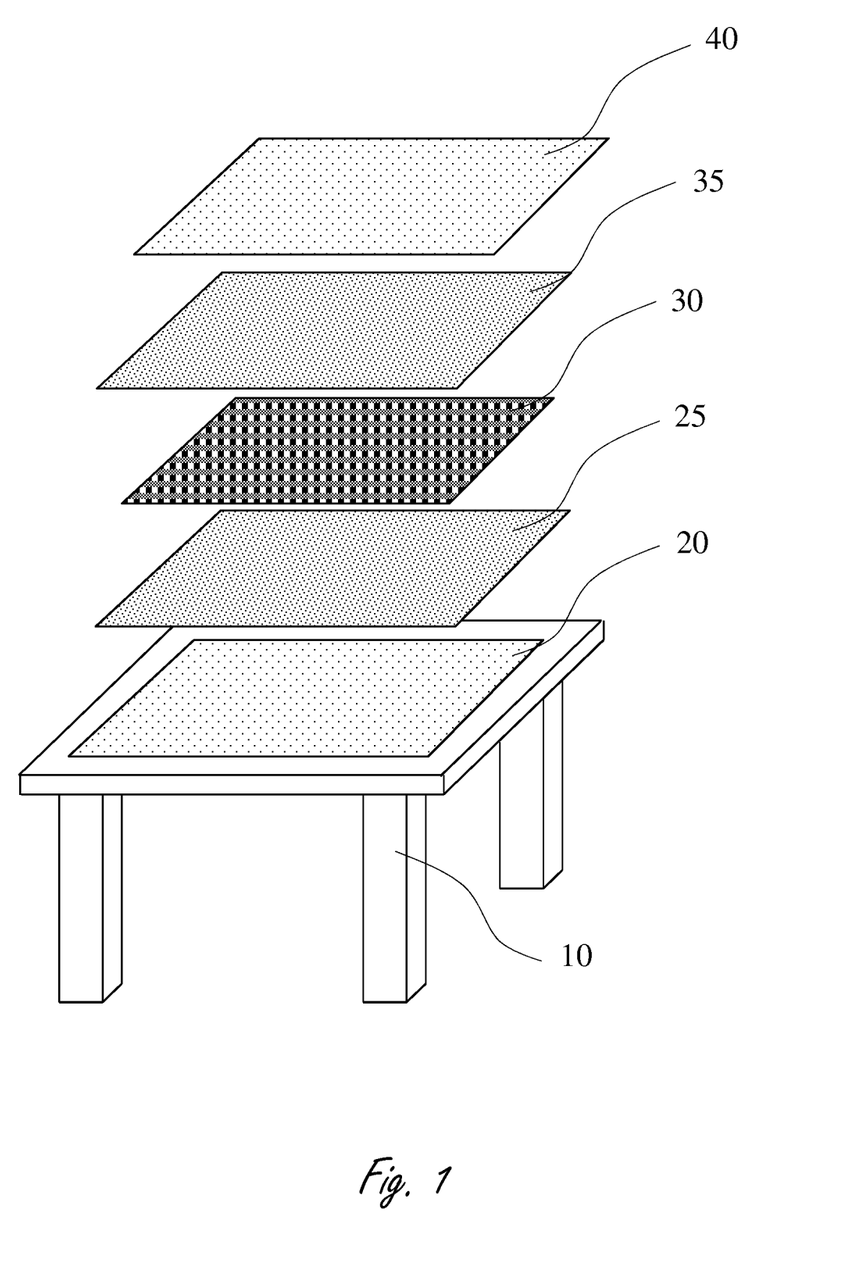
FIG. 1 is a prospective view of a test station table with an exploded electric switchable device.

Reference is now made to FIG. 1, presenting a levelled-up table 10 of a test station and a first cover glass 20, a first layer of adhesive interlayer 25; an electric switchable film 30; a second layer of adhesive interlayer 35 and a second cover glass 40 prepared for an operation of lamination in a schematic view. According to the present invention, firstly, the first cover glass 20 is placed onto the levelled-up table 10.

Figure 2:
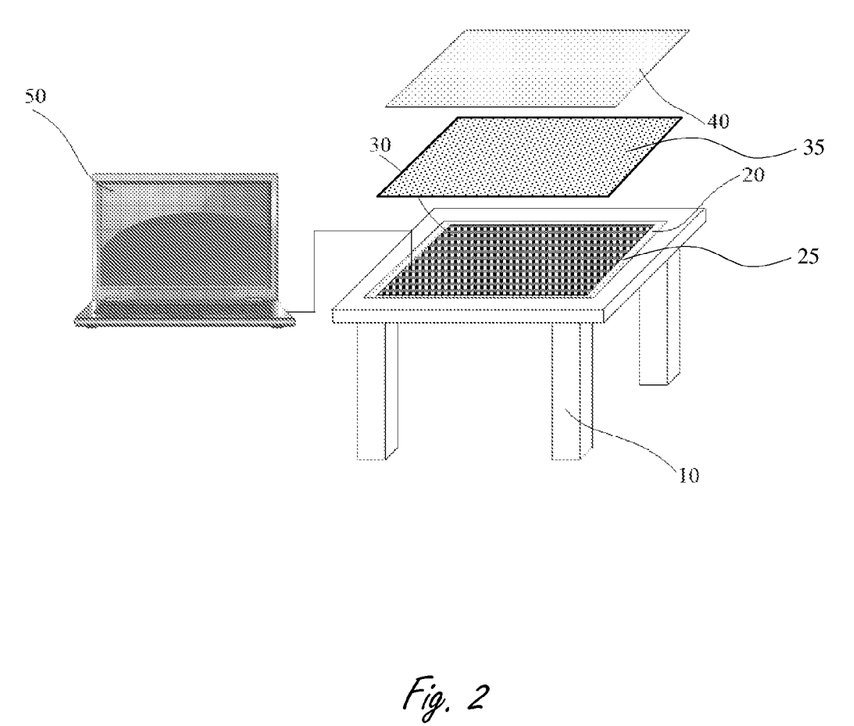
FIG. 2 is a prospective view of a test station where an electric switchable film is spread over a bottom glass.

Reference is now made to FIG. 2, showing a next technological operation of spreading of the electric switchable film 30 over the first layer of adhesive interlayer 25 and the first cover glass 20. According to the present invention, the electric switchable film 30 spread over the first layer of adhesive interlayer 25 and the first cover glass 20 is electrically and optically tested before an operation of lamination. Specifically, electric terminals (not shown) of the electric switchable film 30 are connected to a computerized measuring device 50 which is preprogrammed for applying a square wave of 70 VAC to the aforesaid electric terminals of the electric switchable film 30 at frequency ranging between 25 Hz and 50 Hz, for example, 25 Hz, 32 Hz and 50 Hz. It should be emphasized that a first voltage application is performed with ramping up train of pulses to avoid electric shorts and technological defects of the electric switchable film 30 and to extend the lifetime of the electric switchable device. According to the present invention, the following parameters are subject to inspection: current consumption, resistance of the electric switchable film, capacitance of the electric switchable film, power consumption of the entire glass, power consumption per $m^2$, light transmittance and haze degree. Measuring the abovementioned electric and optical parameters at other voltage and frequencies are also in the scope of the present invention. The computerized measuring device 50 is also preprogrammed for preventing the electric switchable film 30 from applying overvoltage and any DC voltage during the inspecting its electric and optical properties. It should be mentioned that the optical properties such as transmittance and haze degree are inspected by means of through-transmission testing. A source of light and a light detector (not shown) are disposed on opposite sides of an article to be inspected and transmittance and haze degree are measured.

Figure 3:
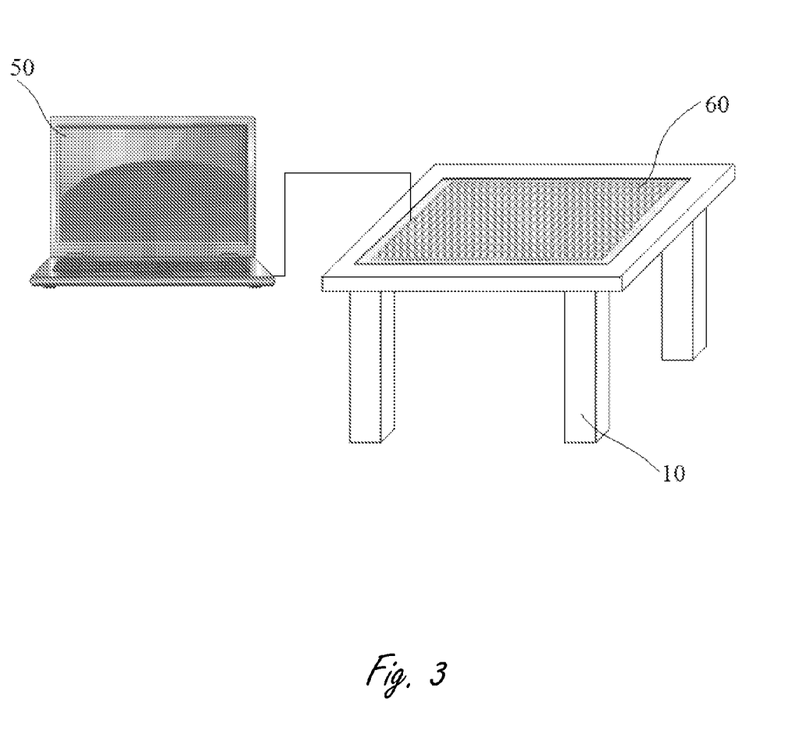
FIG. 3 is a prospective view of a test station with a laminated electric switchable device.

Reference is now made to FIG. 3, illustrating a final inspection of mechanical, optical and electric properties. A laminated electric switchable device 60 is placed on the levelled-up table 10 and its electric terminals (not shown) are connected to the computerized measuring device 50. Similar to an interim inspection described above, in a non-limiting manner, the final inspection includes applying the square wave of 70 VAC to the electric switchable device 60 at frequencies of 25 Hz, 32 Hz and 50 Hz. As emphasized above, current consumption, resistance, capacitance, power consumption of the entire electric switchable device, power consumption per $m^2$, light transmittance and haze degree can be measured at different voltage amplitudes and frequencies, which are in the scope of the presented invention.

It should be emphasized that electric switchable device quality inspection is performed in an individual manner. For this reason, the electric switchable device can include a label identifier on a glass surface or embedded inside. Thus, each electric switchable device is authenticated by means of recognizing outer or inner label identifier. The previously mentioned identifier is recognized in an electromagnetic manner Other methods of label recognition are also in the scope of the present invention. As an example, an RFID tag, a computer chip, an inner or outer graphic label can be detectable visually and/or instrumentally.

Concerning inspection of optical properties of the electric switchable device, time resolved measurements of spectral transmittance dependence provides dynamic haze characteristic describing time resolved haze response to applying AC voltage to the electric switchable device.

Figure 4A:
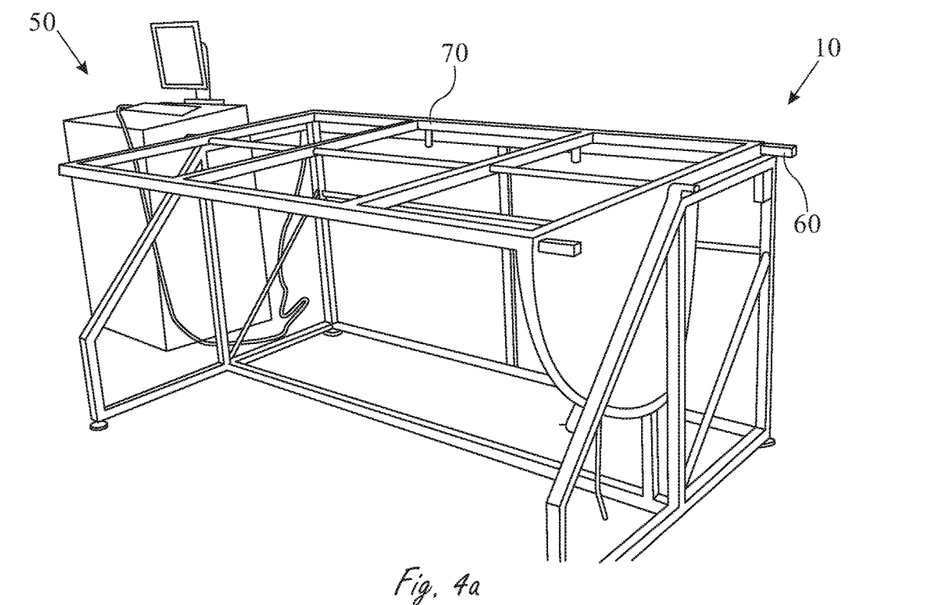
FIGS. 4a and 4b are photographs of an electric switchable device test station in levelled and tilted positions.
Figure 4B:
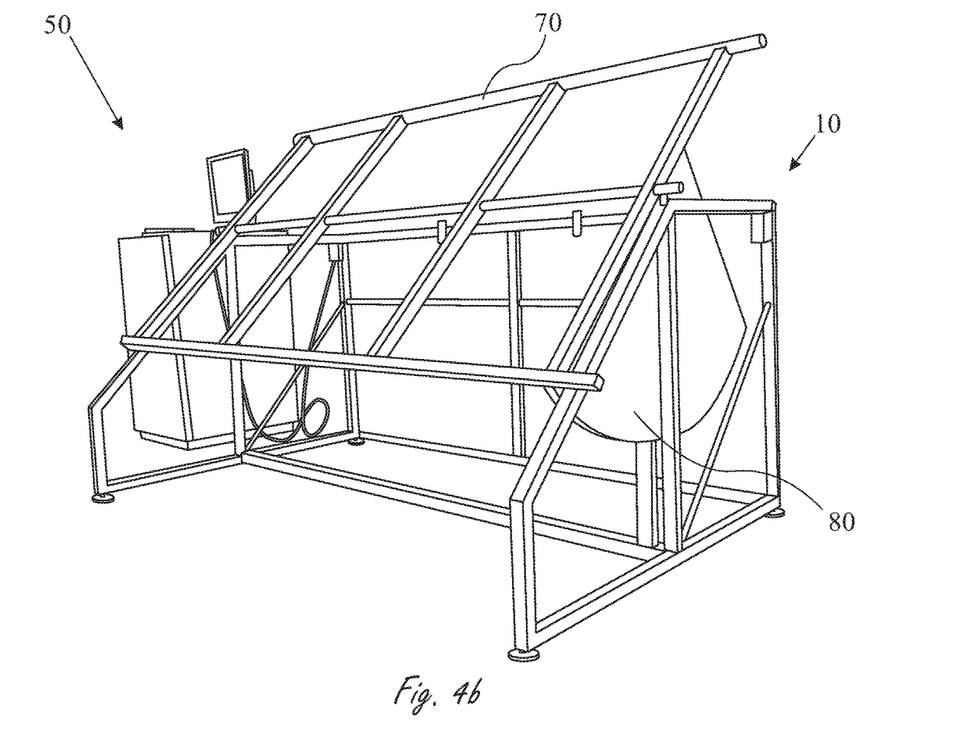

Reference is now made to FIGS. 4a and 4b, presenting the electric switchable device test station, which includes a test table 10, and a computerized measuring device 50. The electric switchable device (not shown) is placed onto a frame 70, which is horizontally or angularly positioned. For convenience frame tilting, the table is provided with a counter balancer 80.

Figure 5A:
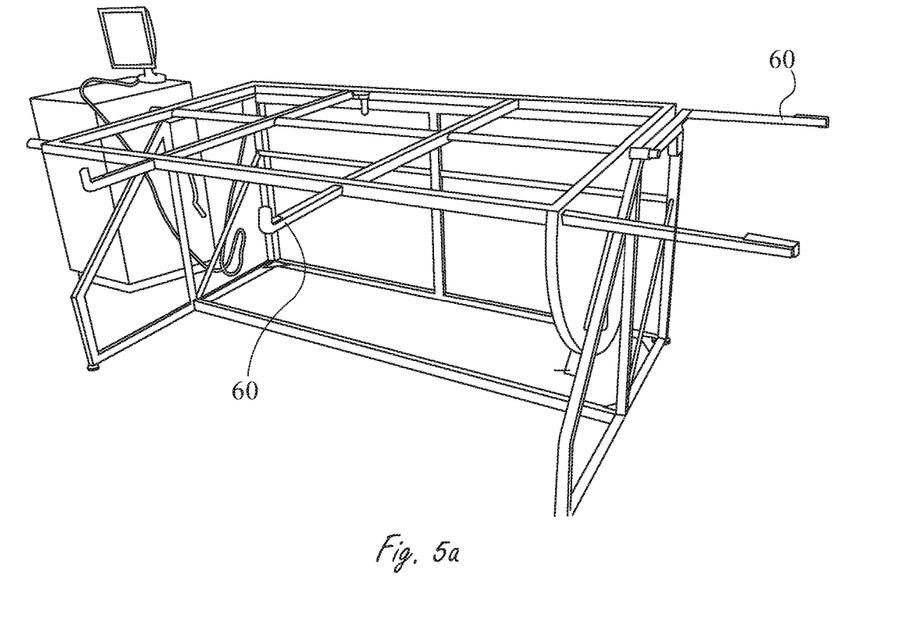
FIGS. 5a and 5b are photographs of an electric switchable device test station in an extended position.
Figure 5B:
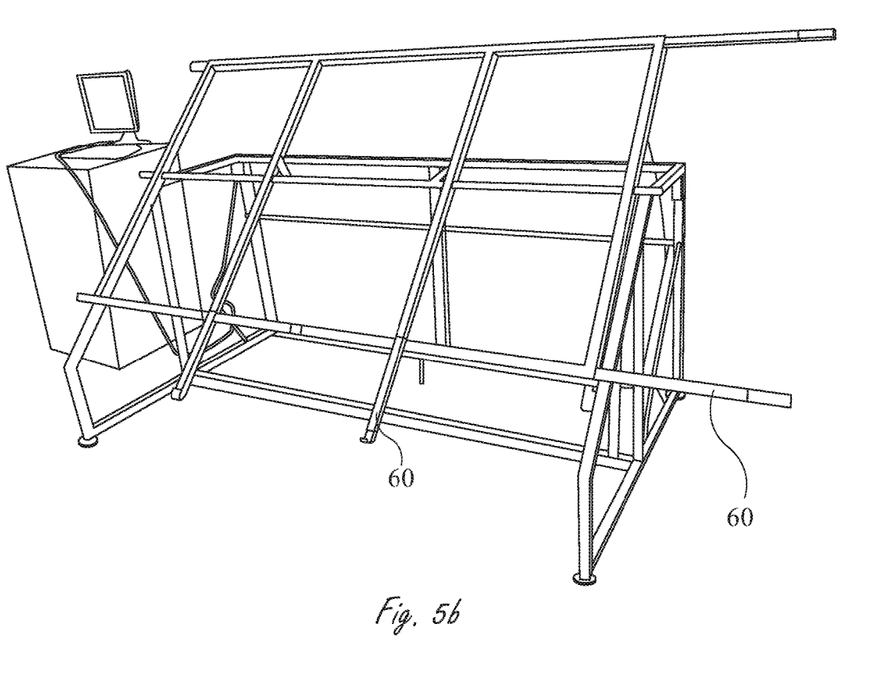

Reference is now made to FIGS. 5a and 5b, presenting the electric switchable device test station with extension bars 60 in an expanded position which provide an option of inspection of electric switchable devices of bigger sizes.

It should be emphasized that members of the frame are provided with led bars back lighting the electric switchable device to be tested.

Figure 6:
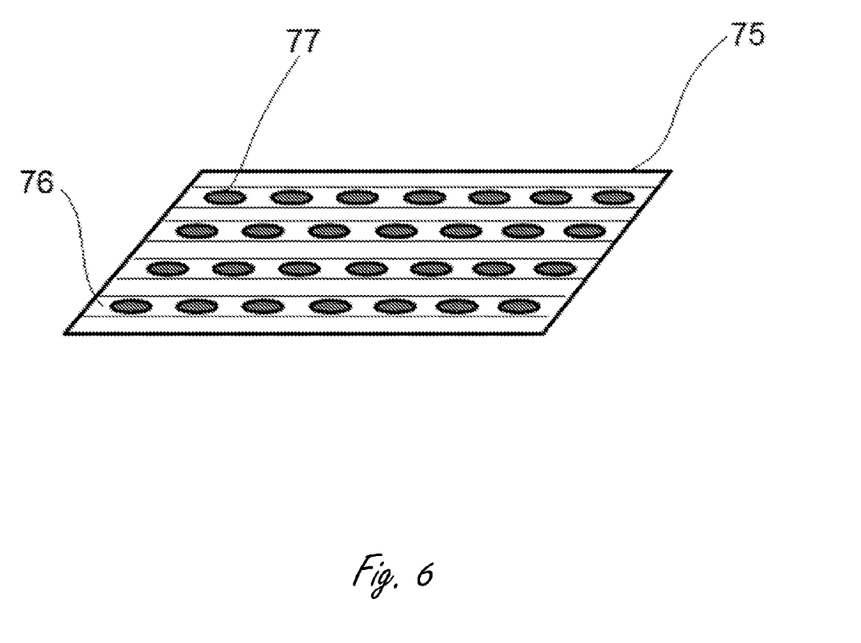
FIG. 6 is a schematic view of backlighting matrix.

Reference is now made to FIG. 6 presenting a backlighting LED matrix, which is designed for substantially uniform backlighting of the electric switchable device of the test table. The previously mentioned matrix 75 comprises a number of bars 76 carrying LEDs 77, which are activated during glass testing. Any film defect or dust particles can be identified in backlight illumination provided by the matrix 75. Backlighting matrix 75 can be covered by a scattering (milk) glass or film to unify illumination provided by the matrix.

Figure 7:
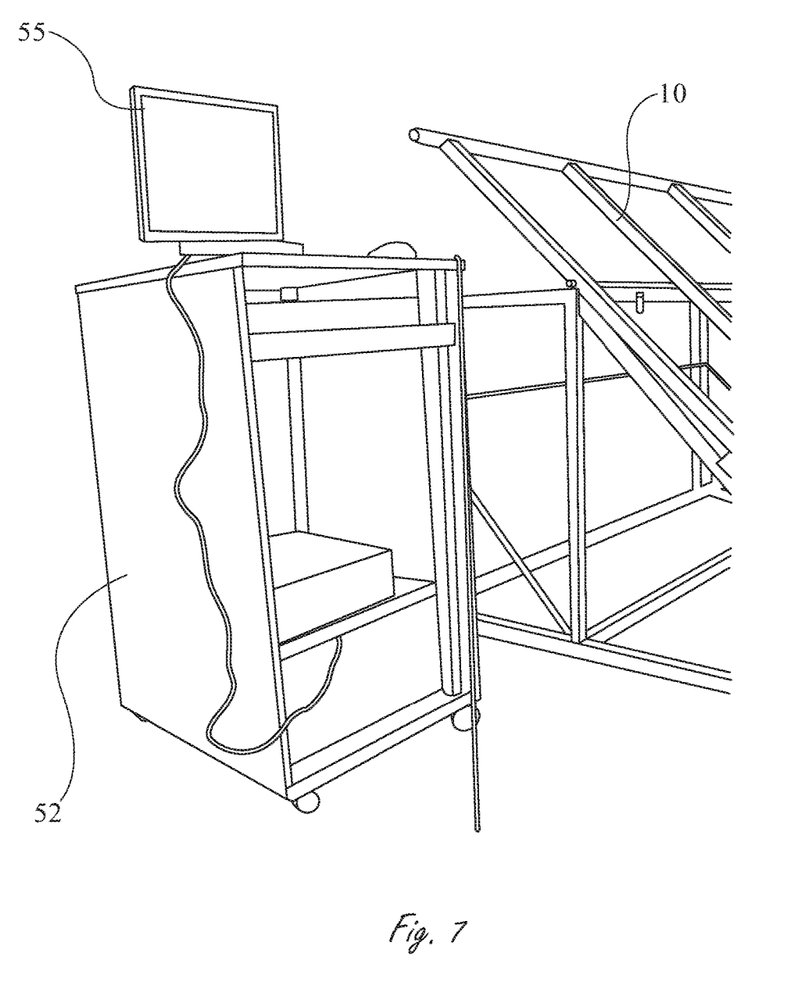
FIG. 7 is a photograph of a computerized measuring device.

Reference is now made to FIG. 7, presenting a computerized measuring device including a main unit 52 and a display 55. In a non-limiting manner, the main unit 55 comprises a generator of square electric waves of frequency ranging between 25 Hz and 50 Hz and means for measuring optical and electrical characteristics of electric switchable devices to be tested.

Figure 8:
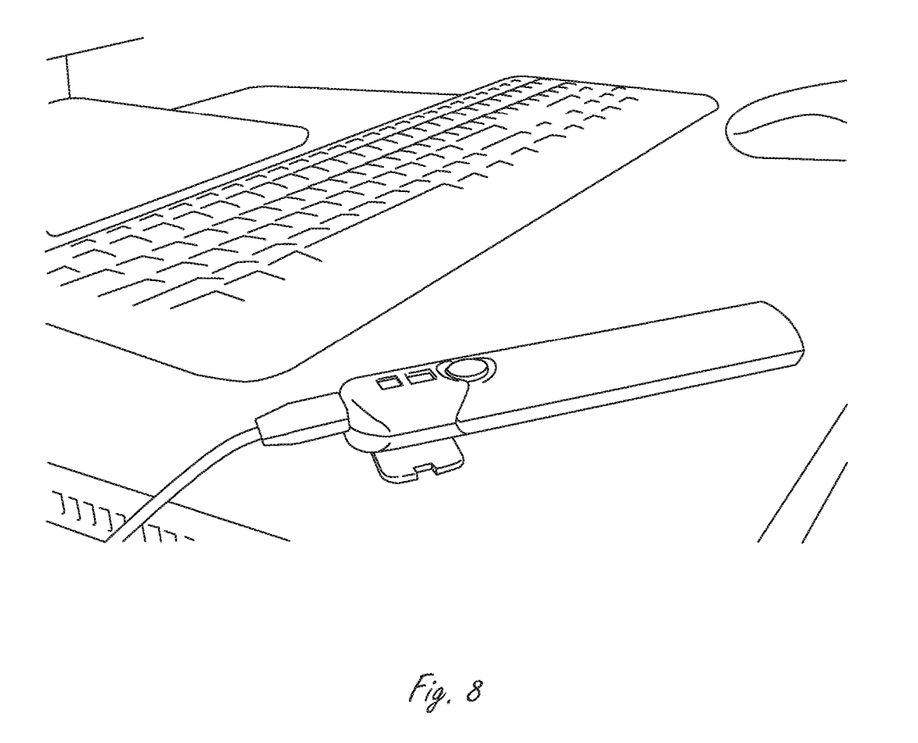
FIG. 8 is a photograph of a handheld optical probe.

Reference is now made to FIG. 8, presenting an optical probe device connected to the computerized measuring device capable to measure the light transmittance and haze of the tested electric switchable film or glass piece. This optical probe is also designed for in-situ inspection of the electric switchable device before and/or after mounting to electric switchable device check operability.

Figure 9:
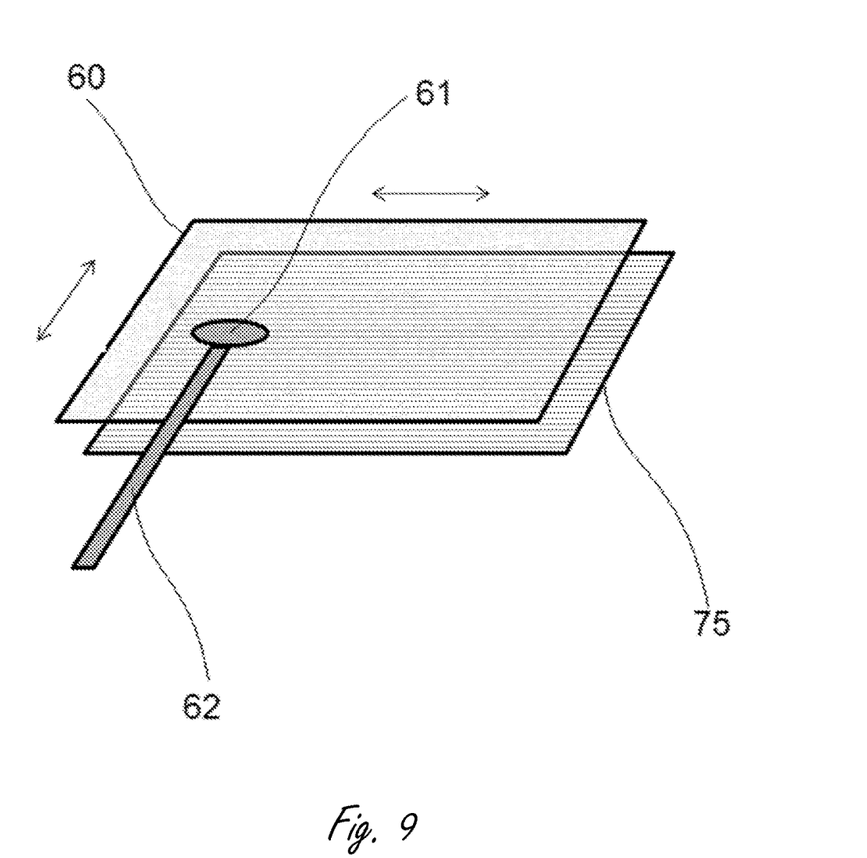
FIG. 9 is a schematic view illustrating optical probe operation.

Reference is now made to FIG. 9, showing a handheld optical probe comprising a detecting portion 61 including, for example, semiconductor optical sensor (not shown) and a handle 62. An operator (not shown) displaces the detecting portion 61 in directions indicated by arrows over the electric switchable device 60, which is backlighted by the matrix 75. Irregularities in optical characteristics give evidences for defects of electric switchable device.

Figure 10:
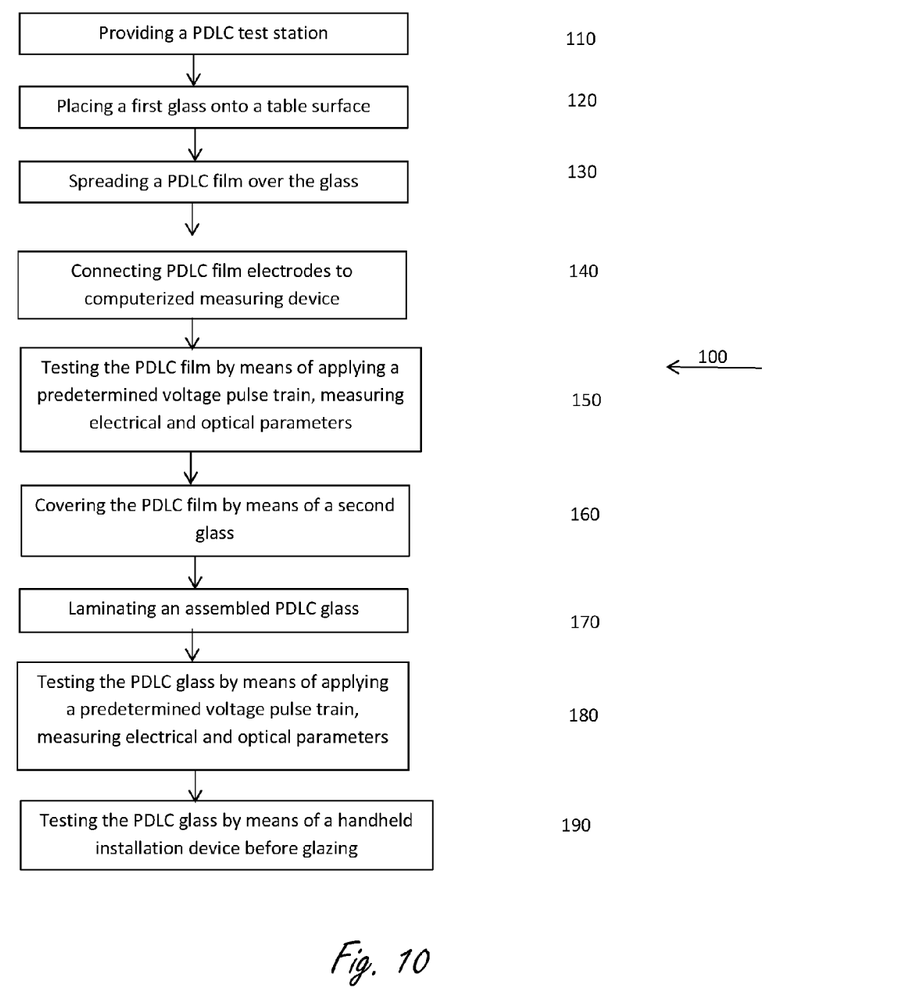
FIG. 10 is a flowchart of a method of quality assessment of an electric switchable device.

Reference is now made to FIG. 10, presenting a flowchart of the described above method of producing switchable electric switchable devices 100, which includes steps 110-180. Specifically, after providing a test station (step 110), a first cover glass and adhesive interlayer film are placed onto a surface of the levelled-up table (step 120). Then, an electric switchable film is spread over the first cover glass (step 130) and electric switchable film electric terminals are connected to a computerized measuring device (step 140). The electric and optical properties of the electric switchable film are inspected by means of applying a predetermined voltage pulse train described above (step 150). After inspection of the electric switchable film (step 150), it is covered by a second cover glass and adhesive interlayer film (step 160), and lamination is performed (step 170). Final inspection of a ready-assembled electric switchable device is performed at step 180 and includes again measurements of current consumption, resistance, capacitance, power consumption of the film piece, power consumption per $m^2$, light transmittance and haze degree. The same parameters are checked in situ before and/or after glazing (step 190). Measuring electric and optical characteristics at all ranges of frequencies is in the scope the present invention.

Figure 11:
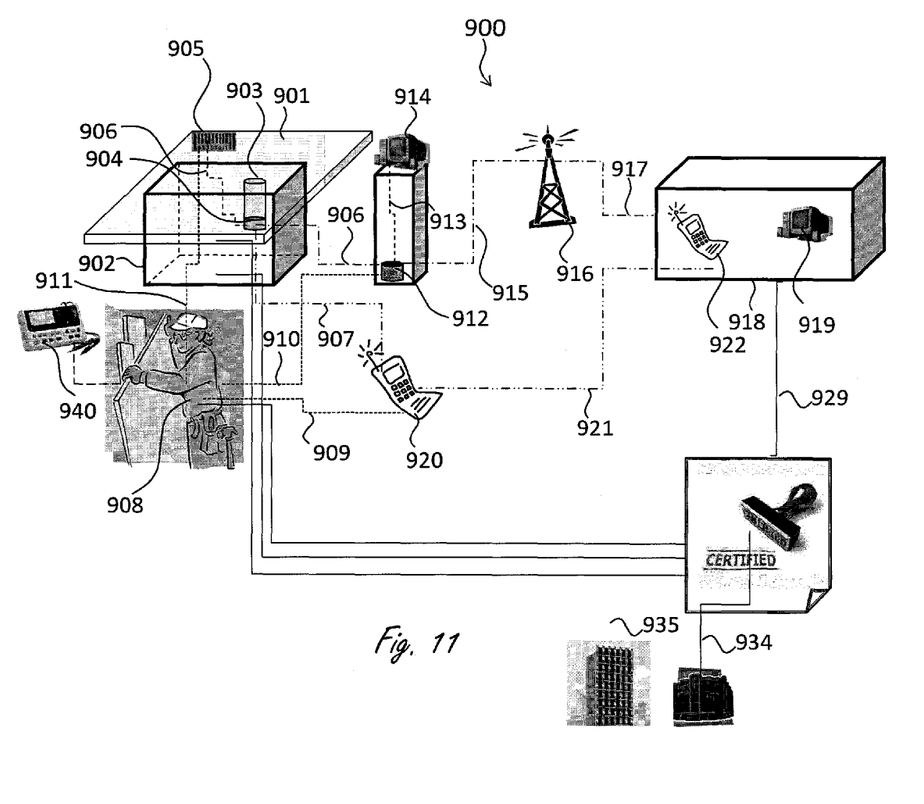
FIG. 11 is schematically illustrating a secured and securing system (900) for ensuring the quality and functioning of a window element and constructions and systems comprising the same.

A reference is now made to FIG. 11, schematically illustrating a secured and securing system (900) for a ensuring the quality and functioning of a window element and constructions and systems comprising the same, including, inter alia, a transparent sheet(s) in connection with at least one electric switchable film, an electric switchable device or the like (901). In an embodiment of the invention, system 900 comprises a glass (901), and glass installing, assembling or manufacturing person (908), a glass installation table (10, 901) in connection with glass analyzing modules (903), glass analysis processing module (914), certificating and/or approving authority (919), such as the electric switchable film producer etc. Hence, according to another embodiment of the invention, the glass is temporarily installed on glass installation table (901). One or more glass analyzing modules (903) are either reversibly movable or stationary affixed in a predefined location in connection with the table. The analysis data is wirelessly or in-line (via a wired communication) transferred (906) from the analyzing equipment(s) (903), via a communicating module (904), to a glass analysis processing module (914), interconnected a communication module (912). Thus, a computerized analysis of a pre-installed glass is provided useful. According to yet another embodiment of the invention, glass 901 is marked with or associated to a barcode, watermark, identifying data or mark thereof, or any other retrievable indicia (905).

Such an identification of the glass provides means for identification of the glass, table (and analysis system), laboratory or analyzing personal (Glass installer 908 for example), authentication of one or more of the follows: the inspected glass, glass's analysis documents, analysis protocol, personal etc.; authorization of one or more of the follows: utilizing the said identified glass, the personal, the analyzing and communicating system etc.; verification of one or more of the follows: glass, electric switchable film or personal ID, analysis data etc.; specification of one or more of the follows: optical properties of the pre-installed glass, electric switchable film such as the optical transmittance and haze, spectroscopy parameters and uniformity thereof; payment monitoring and clearing, namely ensuring payment for the glass and its analysis, glass certification etc.; and certification (929), namely providing identified, securable certification, ensuring, inter alia, the suitability of the pre-installed glass and components thereof to a predefined protocol and standards, the analysis system, the professionalism of the personal for preparing and analyzing the glass, thereby providing said certificate a basis for further technical supporting and/or insuring the installed glass, according to a predefined and an agreed insurance policy (934); ensuring the end client that said glass (901) meets his predefined standards, etc.

To improve reliability of the installed switchable device, an electric diagnostics of the switchable device is performed by a mobile (portable) testing device 940 before installation in situ. The testing device 940 is preprogrammed to measure current consumption, resistance, capacitance and power consumption at different voltage amplitudes and frequencies.

It is according to another embodiment of the present invention wherein the analysis data, glass ID (905, 911), personal identification (909) etc. is transferred by the glass analysis processing module (914) or communicating module (912) thereof to a certificating identity (919). Such a communication is provided e.g., wirelessly, see path 915, 916, and 917.

Alternatively or additionally, the analysis data, glass ID (905) etc. is transferred in a feedback manner form the operator's smartphone (920) to the certificating identity (919), such as described in a communication path 908, 909, 920, 921, and 919. Such a path may comprise a step of communicating (911) smartphone (920) with glass barcode (905) etc. Alternatively or additionally, personal (908) is wirelessly or otherwise communicated (910) with the communication module (912). RFID, Bluetooth and the like are an example to such a communication means and methods.

It is in the scope of the present invention wherein, by means of said smart phone (920), a certificating application is provided. Said application ensures an identified pre-installed glass (901) was prepared according to a predefined protocol and stands within retrievable standards.

It is further in the scope of the present invention wherein, by means of said smart phone (920), an electric switchable device installation tool-box application is provided. Said application enables a personal with respectively limit experience to install an electric switchable film within an identified pre-installed glass (901) easily, intuitively yet in a professional manner according to a predefined protocol such his/her product (901) stands within retrievable standards.

It is according to another embodiment of the present invention a method of producing electric switchable devices is disclosed. The method comprising the steps of providing a re-installed glass (901) by, e.g., providing a first cover glass and a second cover glass; providing an electric switchable film; providing a first layer of adhesive interlayer and a second layer of adhesive interlayer; providing an inspection station further comprising a levelled-up table (902); providing means 903 for inspecting properties of said electric switchable devices selected from the group consisting of electric properties, optical properties, mechanical properties and any combination thereof; placing said first cover glass onto said levelled-up table; spreading a first layer of adhesive interlayer; spreading said PDLC film over the previously placed adhesive interlayer; spreading a second layer of adhesive interlayer; covering said PDLC film by means of said second cover glass; laminating said PDLC film between said first and second cover glasses; and inspecting said glass properties by means of said PDLC inspection station. The inspecting step is potentially performed before and after said step of laminating said electric switchable film.

It is according to another embodiment of the present invention wherein a method of providing a quality assurance for producing electric switchable devices. This method comprises steps of providing an electric switchable device (901); providing an inspection station (914) further comprising a test table (902); means (903) for inspecting properties of said electric switchable devices selected from the group consisting of electric properties, optical properties, mechanical properties and any combination thereof; placing said glass onto said table; and inspecting said properties by means of said inspection station. The inspecting step is potentially performed before and after said step of laminating said electric switchable.

According to the present invention, a method of producing electric switchable devices is disclosed. The aforesaid method comprises the steps of: (a) providing a first cover glass and a second cover glass; (b) providing a PDLC film or any other electrically switchable film; (c) providing a first layer of adhesive interlayer and a second layer of adhesive interlayer; (d) providing an inspection station further comprising: (i) a levelled-up table; (ii) means for inspecting properties of said electric switchable devices selected from the group consisting of electric properties, optical properties, mechanical properties and any combination thereof; (e) placing said first cover glass onto said levelled-up table; (f) spreading a first layer of adhesive interlayer (g) spreading said PDLC film over the previously placed adhesive interlayer; (h) spreading a second layer of adhesive interlayer; (i) covering said PDLC film by means of said second cover glass; (j) laminating said PDLC film between said first and second cover glasses; and (k) inspecting said glass properties by means of said PDLC inspection station.

It is a core feature of the invention to provide the inspecting step is performed before and after said step of laminating said electric switchable film.

According to one embodiment of the present invention, the method comprises a step of projecting extension bars configured for supporting oversized electric switchable devices.

According to another embodiment of the present invention, the method comprises a step of tilting said electric switchable devices.

According to one embodiment of the present invention, the step of inspecting mechanical properties comprises visually inspecting a glass surface and measuring glass overall dimensions.

According to one embodiment of the present invention, the step of inspecting optical properties comprises measuring optical transmittance/haze of the electric switchable device and uniformity thereof over said electric switchable device.

According to one embodiment of the present invention, the step of inspecting optical properties comprises inspecting a haze degree by means of measuring a time resolved spectral dependence of transmittance pertaining to said electric switchable device.

According to one embodiment of the present invention, the step of inspecting optical properties comprises illuminating said electric switchable device by backlight LED.

According to one embodiment of the present invention, the step of illuminating said electric switchable device by backlight is performed by mean of a light source selected from the group consisting of a white light source, a white light source provided with a spectral filter, a laser and any combination thereof.

According to one embodiment of the present invention, the step of inspecting optical properties is performed by at least 5 sensors distributed over a surface of the electric switchable device.

According to one embodiment of the present invention, the step of inspecting optical properties is performed by means of line-by-line scanning.

According to one embodiment of the present invention, the step of inspecting optical properties comprises inspecting specific pixels of the electric switchable film or laminated glass performed by microscopic means. According to one embodiment of the present invention, the step of inspecting electric properties comprises measuring values of electric current, resistance, capacitance and power consumption.

According to one embodiment of the present invention, the step of measuring values of electric current and power consumption is performed by a square wave 70 VAC at frequency ranging between 25 and 50 Hz.

According to one embodiment of the present invention, the initial ramp-up comprises a pulse train of increasing amplitude; pulses of said train are characterized by changeable pulse duration and time interval therebetween.

According to one embodiment of the present invention, the step of measuring values of electric current and power consumption comprise an initial ramp-up at first energizing said electric switchable device.

According to one embodiment of the present invention, the step of initial ramp-up comprises a series of train pulses at an increasing amplitude.

According to one embodiment of the present invention, the electric switchable device is prevented from applying DC voltage.

According to one embodiment of the present invention, the method comprises a step of authenticating said electric switchable device.

According to one embodiment of the present invention, the step of authenticating said electric switchable device is performed by means of recognizing a label identifier on a surface of said electric switchable device or embedded into said electric switchable device.

According to one embodiment of the present invention, the label identifier is an electromagnetically detectable label.

According to one embodiment of the present invention, the label identifier is selected from the group consisting of an RFID tag, a computer chip, a graphic label on a surface of said electric switchable device or therewithin, which is detectable visually and/or instrumentally.

According to one embodiment of the present invention, the step of authenticating said electric switchable device comprises real time reporting malfunction incidents to a manufacturer server in a wireless manner.

According to one embodiment of the present invention, the step of inspecting electric properties is performed before installing said electric switchable device in situ.

According to one embodiment of the present invention, the step of inspecting electric properties performed before installing said electric switchable device in situ is performed by a mobile (portable) testing device.

According to one embodiment of the present invention, a method of quality assurance producing electric switchable devices is disclosed. The aforesaid method comprises the steps of: (a) providing an electric switchable device; (b) providing an inspection station further comprising: (i) a test table; (ii) means for inspecting properties of said electric switchable devices elected from the group consisting of electric properties, optical properties, mechanical properties and any combination thereof; (c) placing said glass onto said table; (d) inspecting said properties by means of said inspection station.

According to one embodiment of the present invention, a test station for inspection of an electric switchable device operative in the method is disclosed.

The invention claimed is:

1. A method of producing electric switchable devices; said method comprising the steps of:
    a. providing a first cover glass and a second cover glass;
    b. providing a PDLC film or any other electrically switchable film;
    c. providing a first layer of adhesive interlayer and a second layer of adhesive interlayer;
    d. providing a PDLC inspection station further comprising:
        i. a levelled-up table;
        ii. means for inspecting properties of said electric switchable devices elected from the group consisting of electric properties, optical properties, mechanical properties and any combination thereof;
    e. placing said first cover glass onto said levelled-up table;
    f. spreading said first layer of adhesive interlayer;
    g. spreading said PDLC film over said first layer of adhesive interlayer;
    h. spreading said second layer of adhesive interlayer;
    i. covering said PDLC film by means of said second cover glass;
    j. laminating said PDLC film between said first and said second cover glasses;
    k. inspecting said properties by means of said PDLC inspection station;
        wherein said inspecting step is performed before and after said step of laminating said PDLC film;
        further wherein said step of inspecting optical properties comprises measuring optical transmittance/haze of the electric switchable device and uniformity thereof over said electric switchable device.

2. The method according to claim 1, comprising at least one step selected from the group consisting of:
    a. projecting extension bars configured for supporting oversized electric switchable devices;
    b. tilting said electric switchable devices; and
    c. any combination thereof.

3. The method according to claim 1, wherein said step of inspecting mechanical properties comprises visually inspecting a glass surface and measuring glass overall dimensions.

4. The method according to claim 1, wherein said step of inspecting optical properties comprises at least one step selected from the group consisting of:
    a. inspecting a haze degree by means of measuring a time resolved spectral dependence of transmittance pertaining to said electric switchable device;
    b. illuminating said electric switchable device by backlight LED;
    c. illuminating said electric switchable device by backlight is performed by mean of a light source selected from the group consisting of a white light source, a white light source provided with a spectral filter, a laser and any combination thereof;
    d. inspecting specific pixels of the electric switchable film or laminated glass performed by microscopic means; and
    e. any combination thereof.

5. The method according to claim 1, wherein said step of inspecting optical properties is performed by at least one selected from the group consisting of:
    a. 5 sensors distributed over a surface of said electric switchable device;
    b. by means of line-by-line scanning;
    c. any combination thereof.

6. The method according to claim 1, wherein said step of inspecting electric properties comprises measuring values of electric current, resistance, capacitance and power consumption.

7. The method according to claim 6, wherein said step of measuring values of electric current and power consumption is performed by a square wave 70 VAC at frequency ranging between 25 and 50 Hz;

further wherein said step of measuring values of electric current and power consumption comprise an initial ramp-up at first energizing said electric switchable device and said initial ramp-up comprises a pulse train of increasing amplitude; pulses of said train are characterized by changeable pulse duration and time interval therebetween.

8. The method according to claim 6, wherein said step of inspecting electric properties is performed before installing said electric switchable device in situ.

9. The method according to claim 8, wherein said step of inspecting electric properties performed before installing said electric switchable device in situ is performed by a mobile (portable) testing device.

10. The method according to claim 1, wherein said electric switchable device is prevented from applying DC voltage.

11. The method according to claim 1, comprising a step of authenticating said electric switchable device.

12. The method according to claim 11, wherein at least one of the following holds true:
 a. said step of authenticating said electric switchable device is performed by means of recognizing a label identifier on a surface of said electric switchable device or embedded into said electric switchable device;
 b. said label identifier is an electromagnetically detectable label;
 c. said label identifier is selected from the group consisting of an RFID tag, a computer chip, a graphic label on a surface of said electric switchable device or therewithin, which is detectable visually and/or instrumentally;
 d. said step of authenticating said electric switchable device comprises real time reporting malfunction incidents to a manufacturer server in a wired or wireless manner.

13. The method according to claim 1, wherein said method is used as a method of quality assurance for producing electric switchable devices.

14. A test station for inspection of an electric switchable device operative in the method of
 a. providing a first cover glass and a second cover glass;
 b. providing a PDLC film or any other electrically switchable film;
 c. providing a first layer of adhesive interlayer and a second layer of adhesive interlayer;
 d. providing a PDLC inspection station further comprising:
  i. a levelled-up table;
  ii. means for inspecting properties of said electric switchable devices elected from the group consisting of electric properties, optical properties, mechanical properties and any combination thereof;
 e. placing said first cover glass onto said levelled-up table;
 f. spreading said first layer of adhesive interlayer;
 g. spreading said PDLC film over said first layer of adhesive interlayer;
 h. spreading said second layer of adhesive interlayer;
 i. covering said PDLC film by means of said second cover glass;
 j. laminating said PDLC film between said first and said second cover glasses;
 k. inspecting said properties by means of said PDLC inspection station;
  wherein said inspecting step is performed before and after said step of laminating said PDLC film;
  further wherein said step of inspecting said properties comprises inspecting a haze degree by means of measuring a time resolved spectral dependence of transmittance pertaining to said electric switchable device.

15. A test station for inspection of an electric switchable device operative in the method of
 a. providing an electric switchable device;
 b. providing an inspection station further comprising:
  i. a test table;
  ii. means for inspecting properties of said electric switchable devices selected from the group consisting of electric properties, optical properties, mechanical properties and any combination thereof;
 c. placing a glass onto said table;
 d. inspecting said properties by means of said inspection station;
 wherein said inspecting step is performed before and after said step of laminating said electric switchable film;
 further wherein said step of inspecting said properties comprises inspecting a haze degree by means of measuring a time resolved spectral dependence of transmittance pertaining to said electric switchable device.

* * * * *